(12) United States Patent
Onishi et al.

(10) Patent No.: US 11,534,050 B2
(45) Date of Patent: Dec. 27, 2022

(54) TURN FIXING MECHANISM PORTION OF ENDOSCOPE APPARATUS AND ENDOSCOPE APPARATUS

(71) Applicant: OLYMPUS CORPORATION, Tokyo (JP)

(72) Inventors: Yoki Onishi, Hachioji (JP); Shigeyasu Kishioka, Kunitachi (JP); Masami Shimizu, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 760 days.

(21) Appl. No.: 16/260,401

(22) Filed: Jan. 29, 2019

(65) Prior Publication Data

US 2019/0150714 A1   May 23, 2019

Related U.S. Application Data

(63) Continuation of application No. PCT/JP2017/034314, filed on Sep. 22, 2017.

(30) Foreign Application Priority Data

Nov. 16, 2016 (JP) .............................. JP2016-223417

(51) Int. Cl.
*A61B 1/00* (2006.01)
*A61B 1/005* (2006.01)
*G02B 23/24* (2006.01)

(52) U.S. Cl.
CPC ...... *A61B 1/00052* (2013.01); *A61B 1/00048* (2013.01); *A61B 1/0052* (2013.01);
(Continued)

(58) Field of Classification Search
CPC ............ A61B 1/00045; A61B 1/00048; A61B 1/00052; A61B 1/00064; A61B 1/00066;
(Continued)

(56) References Cited

U.S. PATENT DOCUMENTS 5,287,845 A * 2/1994 Faul .......................... A61B 1/12
600/156
2002/0112319 A1   8/2002 Kida
(Continued)

FOREIGN PATENT DOCUMENTS

CN   101660566 A   3/2010
CN   201779136 U   3/2011
(Continued)

OTHER PUBLICATIONS

International Search Report dated Oct. 24, 2017 issued in PCT/JP2017/034314.

*Primary Examiner* — Ryan N Henderson
(74) *Attorney, Agent, or Firm* — Scully, Scott, Murphy & Presser, P.C.

(57) ABSTRACT

A turn fixing mechanism portion of an endoscope apparatus includes: a turning portion connected to a turning unit turnably disposed; a fixed portion configured to turnably support the turning portion; an elastic member interposed between the turning portion and the fixed portion; and a holding member configured to fix a turned position of the turning unit by pressing the turning portion toward a side of the fixed portion to compress the elastic member in a turning axis direction to generate a predetermined frictional force.

4 Claims, 6 Drawing Sheets

(52) U.S. Cl.
CPC ...... *A61B 1/00066* (2013.01); *A61B 1/00147* (2013.01); *G02B 23/2476* (2013.01)

(58) Field of Classification Search
CPC ..... A61B 1/005; A61B 1/0051; A61B 1/0052; A61B 1/0053; A61B 1/0055; A61B 1/0056; A61B 1/0057; A61B 1/0058; A61B 1/00121; A61B 1/00195
See application file for complete search history.

(56) References Cited

U.S. PATENT DOCUMENTS

| | | | |
|---|---|---|---|
| 2007/0188604 A1* | 8/2007 | Miyamoto | A61B 1/00052 348/65 |
| 2009/0247828 A1* | 10/2009 | Watanabe | A61B 1/00039 600/131 |
| 2010/0043175 A1 | 2/2010 | Wang et al. | |
| 2017/0188795 A1* | 7/2017 | Ouyang | G02B 23/2484 |

FOREIGN PATENT DOCUMENTS

| | | | | |
|---|---|---|---|---|
| CN | 102777487 A | | 11/2012 | |
| CN | 104825125 A | | 8/2015 | |
| JP | 2002-021412 A | | 1/2002 | |
| JP | 2003-148451 A | | 5/2003 | |
| JP | 2005-237513 A | | 9/2005 | |
| JP | 2006-271688 A | | 10/2006 | |
| JP | 2008-275081 A | | 11/2008 | |
| JP | 2012045045 A | * | 3/2012 | ......... A61B 1/00078 |
| JP | 2015134072 A | * | 7/2015 | |

\* cited by examiner

TURN FIXING MECHANISM PORTION OF ENDOSCOPE APPARATUS AND ENDOSCOPE APPARATUS

CROSS REFERENCE TO RELATED APPLICATION

This application is a continuation application of PCT/JP2017/034314 filed on Sep. 22, 2017 and claims benefit of Japanese Application No. 2016-223417 filed in Japan on Nov. 16, 2016, the entire contents of which are incorporated herein by this reference.

BACKGROUND OF THE INVENTION

1. Field of the Invention

The present invention relates to a turn fixing mechanism portion of an endoscope apparatus including an insertion portion inserted into a subject, and to the endoscope apparatus.

2. Description of the Related Art

An endoscope apparatus is introducible from outside to inside of a living body or a structure and is for picking up an optical image in order to observe a part difficult to observe such as inside of the living body or inside of the structure. The endoscope apparatus has been used in, for example, a medical field or an industrial field.

A portable endoscope apparatus has been proposed which has a structure in which a display apparatus configured to visualize an image of an object for display is disposed on an operation portion in order to simplify the endoscope apparatus.

As such a portable endoscope apparatus, an apparatus is known which is integrally provided with a display screen configured to display an observation target in real time at hand while an operator is grasping and operating the apparatus as disclosed in, for example, Japanese Patent Application Laid-Open Publication No. 2005-237513 and Japanese Patent Application Laid-Open Publication No. 2006-271688.

Conventional endoscope apparatuses as disclosed in Japanese Patent Application Laid-Open Publication No. 2005-237513 and Japanese Patent Application Laid-Open Publication No. 2006-271688 have a structure in which for example, the display apparatus is turnable with respect to the operation portion, or a monitor portion of the display apparatus can be turned for a raising operation, so that a user can observe an endoscope image at a desired position.

SUMMARY OF THE INVENTION

A turn fixing mechanism portion of an endoscope apparatus according to an aspect of the present invention includes: a turning portion connected to a turning unit turnably disposed, the turning portion including a first hole; a fixed portion including a projecting portion configured to be inserted into the first hole, and a recessed portion formed around the projecting portion, the recessed portion having a predetermined depth; an elastic member disposed in the recessed portion and held between the recessed portion and the turning portion; a holding member configured to fix a turned position of the turning unit by pressing the turning portion toward a side of the fixed portion to cause the turning portion to abut the projecting portion, and by crushing the elastic member by the turning portion by a predetermined amount to generate a predetermined frictional force; a second hole formed at the holding member; and a fastening member configured to be inserted into the second hole, and to fix the holding member to the projecting portion.

A turn fixing mechanism portion of an endoscope apparatus according to another aspect of the present invention includes: a turning portion connected to a turning unit turnably disposed; a fixed portion configured to turnably support the turning portion; an elastic member interposed between the turning portion and the fixed portion; and a holding member configured to fix a turned position of the turning unit by pressing the turning portion toward a side of the fixed portion to compress the elastic member in a turning axis direction to generate a predetermined frictional force; a first surface formed on the turning portion, the first surface being in contact with the elastic member and having a first surface roughness; and a second surface formed on the turning portion, the second surface being in contact with the elastic member and having a second surface roughness different from the first surface roughness.

A turn fixing mechanism portion of an endoscope apparatus according to yet another aspect of the present invention includes: a turning portion connected to a turning unit turnably disposed; a fixed portion including an equipping portion to which the turning portion is equipped, and a recessed portion formed around the equipping portion, the recessed portion having a predetermined depth; an elastic member disposed in the recessed portion and held between the recessed portion and the turning portion; a holding member configured to fix a turned position of the turning unit by pressing the turning portion toward a side of the fixed portion to cause the turning portion to abut the equipping portion, and by crusing the elastic member by the turning portion by a predetermined amount to generate a predetermined frictional force; a hole formed at the holding member: and a fastening member inserted into the hole, and configured to fix the holding member to the equipping member.

An endoscope apparatus according to an aspect of the present invention includes: a turn fixing mechanism portion including: a turning portion connected to a turning unit turnably disposed, the turning portion including a first hole; a fixed portion including a projecting portion configured to be inserted into the first hole, and a recessed portion formed around the projecting portion, the recessed portion having a predetermined depth; an elastic member disposed in the recessed portion and held between the recessed portion and the turning portion; a holding member configured to fix a turned position of the turning unit by pressing the turning portion toward a side of the fixed portion to cause the turning portion to abut the projecting portion, and by crushing the elastic member by the turning portion by a predetermined amount to generate a predetermined frictional force; a second hole formed at the holding member; and a fastening member configured to be inserted into the second hole, and to fix the holding member to the projecting portion; and an operation portion on which the turning unit is turnably disposed.

DETAILED DESCRIPTION OF THE PREFERRED EMBODIMENT(S)

A preferable embodiment of the present invention will be described below with reference to the drawings. Note that in each figure to be used for the description below, the scale of each component is made different in order to show each component in a recognizable size in the figure, and the present invention shall not be limited only to the number of components drawn in the figures, the shapes of the components, the ratio of the sizes of the components, and the relative positional relationship between respective components.

The description below may be made with the vertical direction as seen facing the paper surface of a figure as an upper portion and a lower portion of a component.

Figure 1:
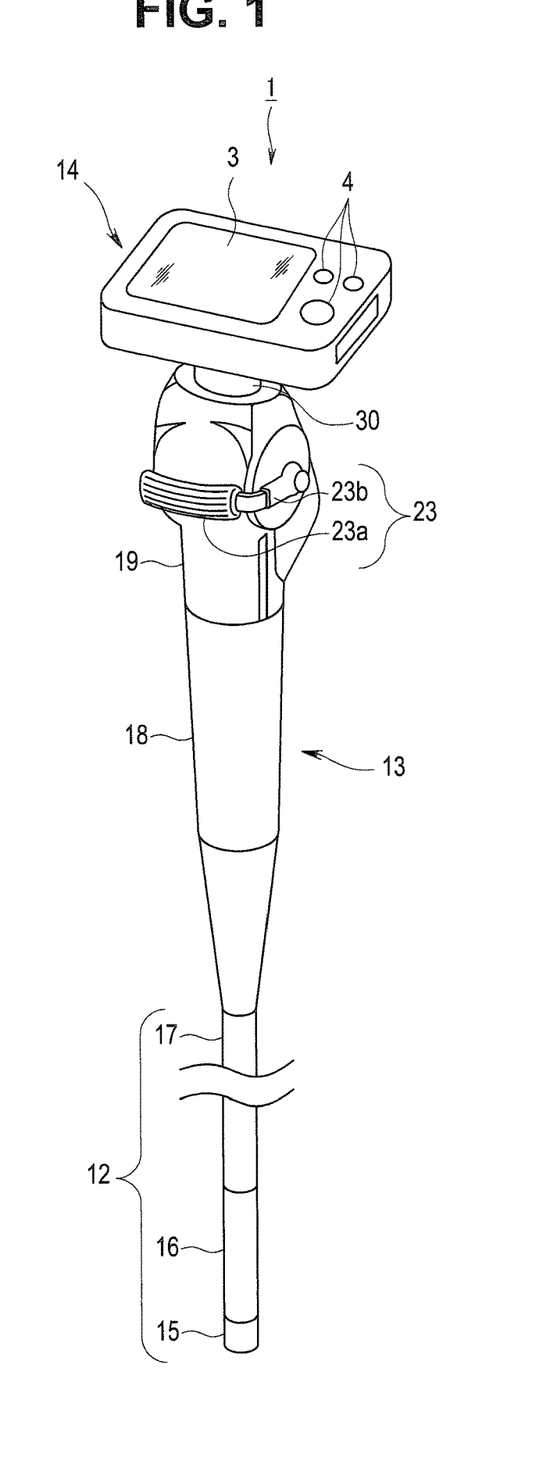
FIG. 1 is a perspective view showing an overall structure of an endoscope apparatus.
Figure 2:
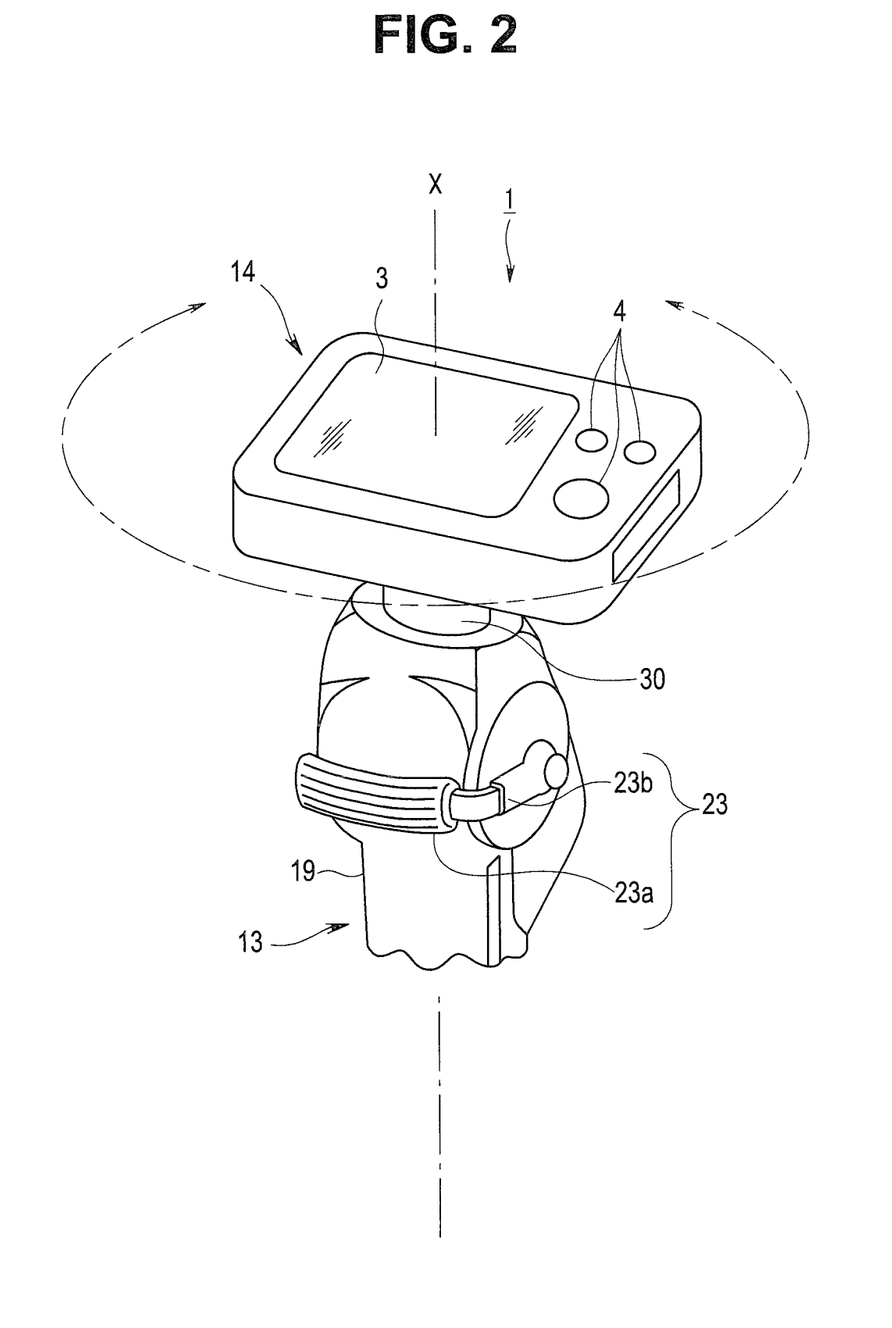
FIG. 2 is a perspective view showing in an enlarged size a display apparatus disposed on an operation portion of the endoscope apparatus.
Figure 3:
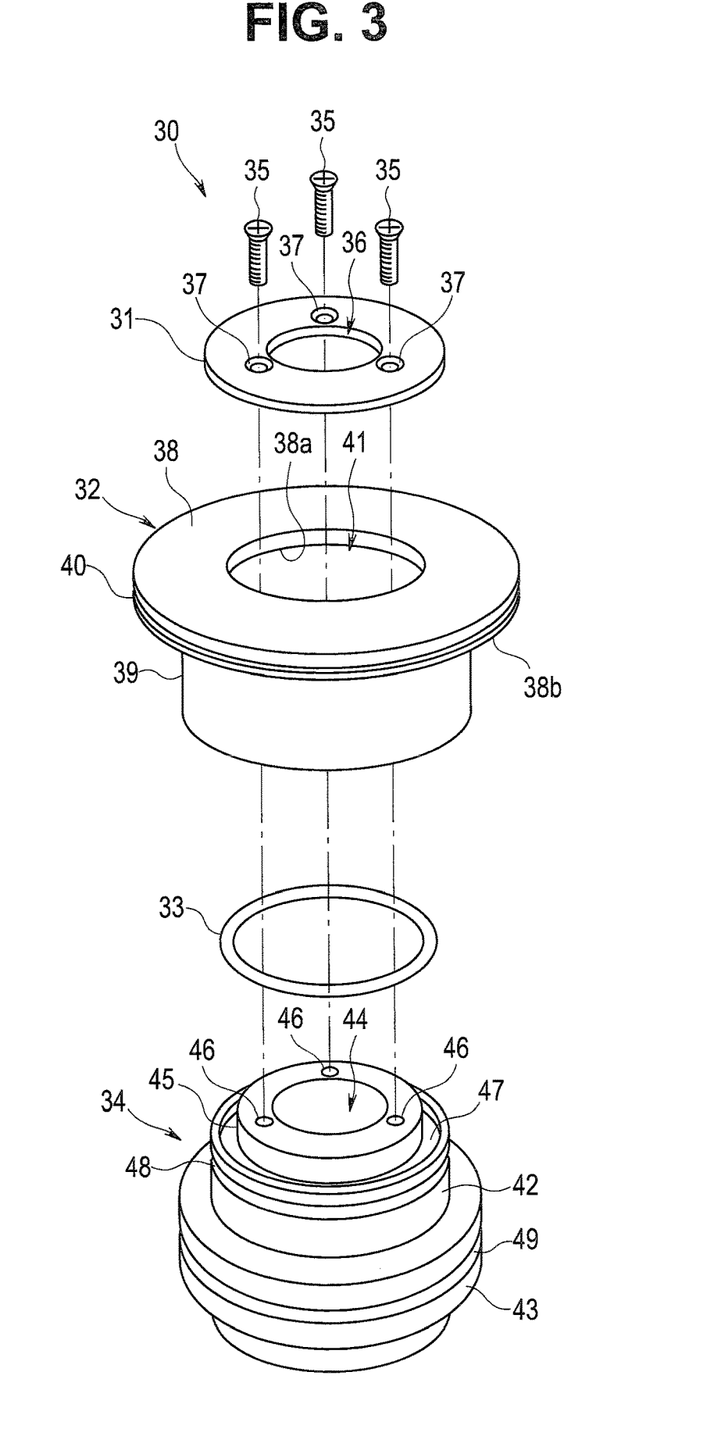
FIG. 3 is a disassembled perspective view showing a structure of a turn fixing mechanism portion of the endoscope apparatus.
Figure 4:
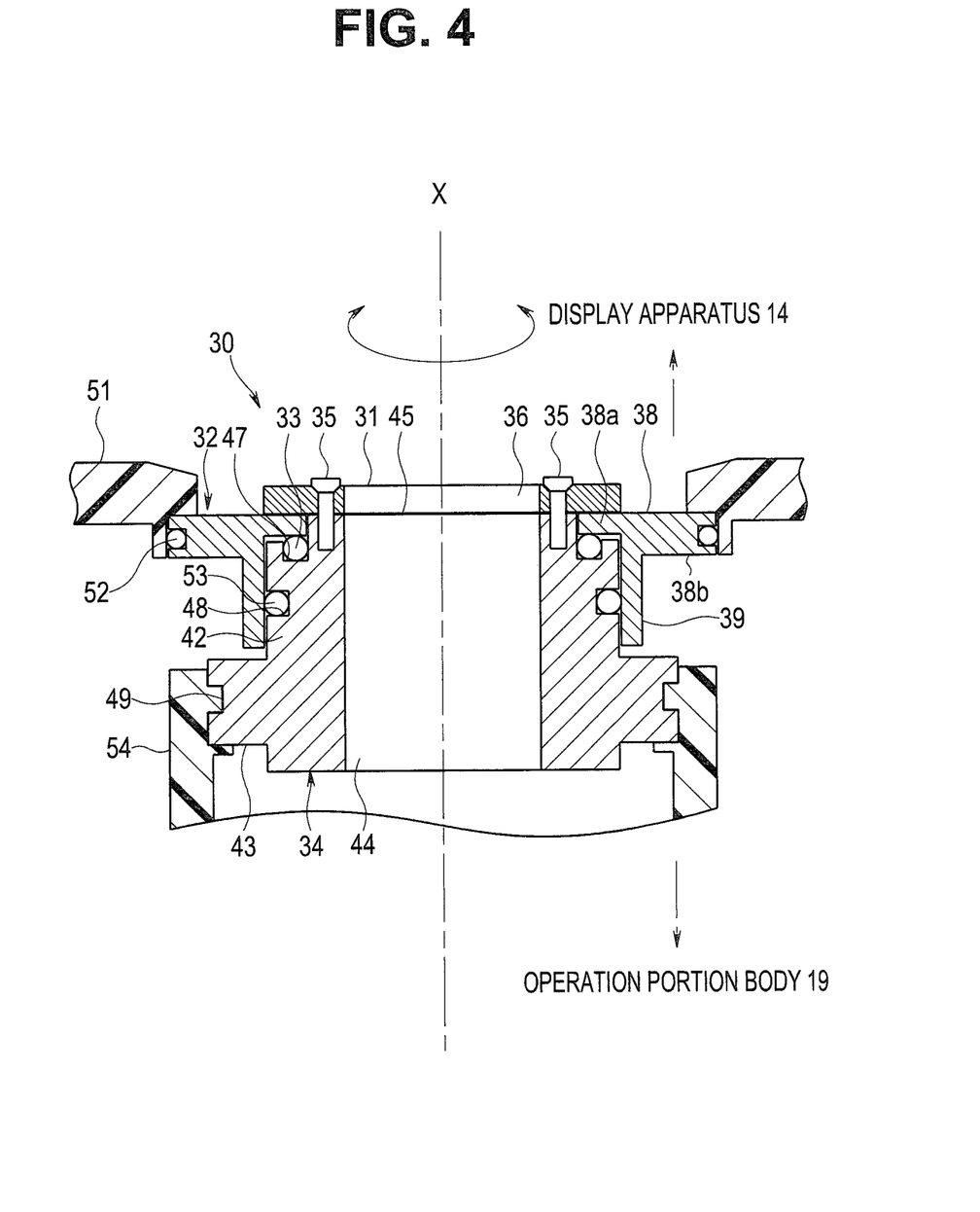
FIG. 4 is a sectional view showing a structure of the turn fixing mechanism portion of the endoscope apparatus.
Figure 5:
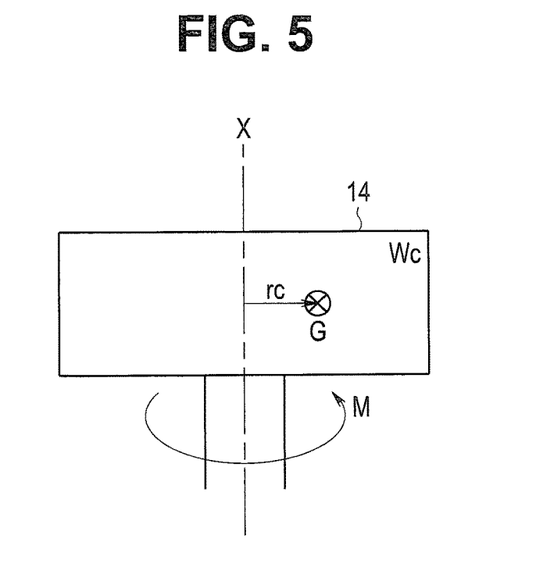
FIG. 5 is a schematic diagram for explaining turning due to the self-weight of the display apparatus of the endoscope apparatus.
Figure 6:
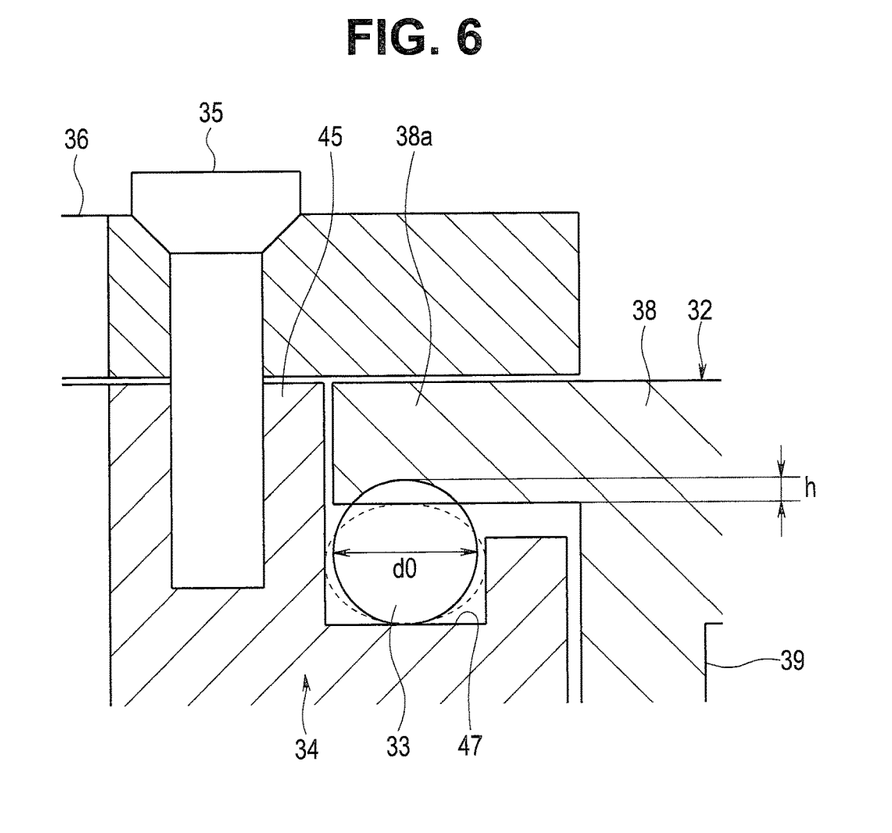
FIG. 6 is a schematic sectional view for explaining a crushing rate (compression rate) of a frictional force generating member of the endoscope apparatus.

FIG. 1 is a perspective view showing an overall structure of an endoscope apparatus, FIG. 2 is a perspective view showing in an enlarged size a display apparatus disposed on an operation portion, FIG. 3 is a disassembled perspective view showing a structure of a turn fixing mechanism portion, FIG. 4 is a sectional view showing a structure of the turn fixing mechanism portion, FIG. 5 is a schematic diagram for explaining turning due to the self-weight of the display apparatus, and FIG. 6 is a schematic sectional view for explaining a crushing rate (compression rate) of a frictional force generating member.

First, an endoscope apparatus according to one aspect of the present invention will be described below. Note that although the embodiment exemplifies an endoscope apparatus introduced into a bronchus or the like, no limitation is imposed, and the embodiment is also a technique applicable to various endoscope apparatuses regardless of the medical field or the industrial field.

As shown in FIGS. 1 and 2, an endoscope apparatus 1 of the embodiment has main portions composed of an insertion portion 12 inserted into a site to be examined in a body cavity which is a subject, an operation portion 13 continuously provided to a proximal end side of the insertion portion 12, and a display apparatus 14 which is a camera unit disposed at an upper end of the operation portion 13 and serves as a turning unit here.

The insertion portion 12 is formed in an elongated shape with flexibility, and has main portions composed of a rigid distal end portion 15 positioned on a distal end side, a bending portion 16 continuously provided to a proximal end side of the distal end portion 15, and a flexible portion 17 continuously provided to a proximal end side of the bending portion 16. The operation portion 13 has main portions composed of a grasping portion 18 grasped by an operator, and an operation portion body 19 continuously provided above the grasping portion 18.

Note that the endoscope apparatus 1 may have a structure in which the grasping portion 18 is provided with a treatment instrument insertion opening for inserting/extracting a treatment instrument such as forceps into/from the body cavity through a treatment instrument channel (not shown) disposed inside the insertion portion 12.

For example, a white light emitting diode (LED) which is illumination means and an illumination portion configured to supply illumination light for illuminating the subject is disposed in the grasping portion 18. Light emitted by the LED (light for illumination) is transmitted by an optical fiber inserted into the insertion portion 12, and emitted from an illumination window provided in the distal end portion 15 toward the site to be examined (neither is shown).

An image pickup device (not shown) composed of a CCD, a CMOS, or the like which is image pickup means and an image pickup portion configured to pick up an image of the site to be examined is disposed in the operation portion body 19. Note that the image pickup device composes the image pickup portion serving as the image pickup means. Note that the image pickup device may be disposed in the display apparatus 14.

The endoscope apparatus 1 may have a structure in which the operation portion body is provided with a suction pipe sleeve (not shown) used in sucking fluids such as bodily fluids and sputum from inside the body cavity so that a suction apparatus (not shown) may be freely connectable to the suction pipe sleeve through a tube.

Note that the operation portion body 19 is provided with a ventilation pipe sleeve not shown which is used to feed air into the insertion portion 12, the operation portion 13, and the display apparatus 14 in water leakage inspection of the endoscope apparatus 1.

An air supply apparatus is freely connectable to the ventilation pipe sleeve (not shown) through a tube not shown. A user as the operator can inspect water leakage of the endoscope apparatus 1 by operating the air supply apparatus to feed air in water from the ventilation pipe sleeve into the endoscope apparatus 1.

The operation portion body 19 is provided with a bending operation lever 23 for bending the bending portion 16 in, for example, the vertical direction via a bending operation wire (not shown) inserted into the insertion portion 12. The bending operation lever 23 is provided at a position on a near side of the user and in proximity to the grasping portion 18 so as to be operated by, for example, the left hand thumb of the operator grasping the grasping portion 18.

As shown in FIG. 2, the display apparatus 14 is turnably connected around a turning axis X which is an axis in a longitudinal direction of the endoscope apparatus 1 (the operation portion body 19 of the operation portion 13) via a turn fixing mechanism portion 30 of the embodiment described later in the upper portion of the operation portion body 19. The display apparatus 14 has a substantially rectangular parallelepiped shape which is a box shape, and has a monitor portion 3 configured to display an endoscope image on an upper surface portion.

A removable battery, a video processing control board, a memory socket having a waterproof structure to which a storage medium can be freely attached, and the like are disposed in the display apparatus 14 (none is shown).

The display apparatus 14 is provided with various switches for operating power-on/off, still image recording, video recording, and the like on a lateral side of the monitor portion 3 on the upper surface.

Next, a structure of the turn fixing mechanism portion 30 of the endoscope apparatus 1 for making the display apparatus 14 turnable with respect to the operation portion body 19 will be described below in detail.

As shown in FIG. 3, the turn fixing mechanism portion 30 of the embodiment is composed of a holding member 31, a turning mount 32 as a turning portion, a frictional force generating member 33 which is an elastic member, for example, an O-shaped ring here, and a fixed mount 34 as a fixed portion.

Here, the holding member 31 is a discoid plate body with a circular hole portion 36 formed at the center. Screw holes 37, the number of which is three here, allowing insertion of the respective fixing screws 35 are formed in the holding member 31 around the hole portion 36 at substantially equal intervals.

The turning mount 32 is a substantially cylindrical body which has a large-diameter plate portion 38 in a discoid shape with an inward flange portion 38a and an outward flange portion 38b formed on the upper side, and a small-diameter cylindrical portion 39 in a cylindrical shape extended and provided downward from the large-diameter plate portion 38. A hole portion 41 having an outer diameter smaller than an outer diameter of the holding member 31 is formed at a center of the turning mount 32.

Note that a recessed circumferential groove 40 is formed on an outer circumference of the large-diameter plate portion 38. The circumferential groove 40 is equipped with an O-shaped ring 52 which is a packing for keeping watertightness with an exterior member 51 of the display apparatus 14 fitting the turning mount 32 (see FIG. 4).

The fixed mount 34 is a cylindrical body with a large-diameter portion 43 provided in the middle of a small-diameter portion 42, and has a through-hole 44 with a hole diameter substantially equal to the hole diameter of the hole portion 36 of the holding member 31 formed at the center. Note that the hole portion 36 of the holding member 31 and the through-hole 44 are for allowing insertion of various signal lines or the like from the operation portion body 19 toward the side of the display apparatus 14. The hole portion 36 and the through-hole 44 may not necessarily have a substantially equal hole diameter.

An annular projecting portion 45 having a further smaller diameter is formed in the upper portion of the small-diameter portion 42. The projecting portion 45 has an outer diameter substantially equal to or slightly smaller than the hole diameter of the inward flange portion 38a formed on the large-diameter plate portion 38 of the turning mount 32, and has screw holes 46, the number of which is three here, to which the fixing screws 35 are screwed formed on an upper surface portion around an opening portion of the through-hole 44 at substantially equal intervals.

A circular recessed portion 47 having an angled-U shape in section in which the frictional force generating member 33 is placed is formed around the projecting portion 45. Note that an outer circumference surface on the upper side situated outward of the recessed portion 47 of the small-diameter portion 42 is formed lower than the surface of the projecting portion 45 toward the lower side so that a step may be made by a thickness of the outward flange portion 38b of the large-diameter plate portion 38.

Note that the small-diameter portion 42 has an outer diameter on the upper side of the large-diameter portion 43 substantially equal to or slightly smaller than the hole diameter of the hole portion 41 of the turning mount 32, and is turnably equipped with the small-diameter cylindrical portion 39 of the turning mount 32 in an externally inserted manner.

At the time, a circumferential groove 48 is formed which is equipped with an O-shaped ring 53 (see FIG. 4) as a watertight packing for keeping watertightness between the turning mount 32 and the fixed mount 34.

Note that a recessed circumferential groove 49 is formed on the outer circumference of the large-diameter portion 43. An exterior member 54 of the operation portion body 19 fitting the fixed mount 34 fits and is fixed to the circumferential groove 49 with an adhesive or the like in a state where watertightness is kept (see FIG. 4).

In the turn fixing mechanism portion 30 structured as described above, as shown in FIG. 4, the turning mount 32 is equipped on the fixed mount 34, and then the holding member 31 is fixed to the fixed mount 34 by the fixing screws 35 while pressing the turning mount 32 from above toward the direction of the fixed mount 34 along the longitudinal direction of the operation portion 13 (the turning axis X described above).

In the state, the inward flange portion 38a formed on the large-diameter plate portion 38 of the turning mount 32 is in contact with the frictional force generating member 33 on the lower surface, and abuts the holding member 31 on the upper surface to be held between the frictional force generating member 33 and the holding member 31. Therefore, the turning mount 32 of the turn fixing mechanism portion 30 is equipped turnably around the rotation axis X in a state where the lower surface of the inward flange portion 38a receives frictional force of the frictional force generating member 33.

That is, the turn fixing mechanism portion 30 enters a state where the turning mount 32 fixed to the display apparatus 14 is sandwiched between the holding member 31 and the frictional force generating member 33 in a direction along the rotation axis X, and the fixed mount 34 is fixed to the operation portion body 19. Thus, the display apparatus 14 is configured to be turnable around the rotation axis X with respect to the operation portion body 19 in a state of receiving a predetermined frictional force from the frictional force generating member 33.

Here, an example structure will be described in which the turn fixing mechanism portion 30 described above generates the predetermined frictional force against turning of the display apparatus 14.

As shown in FIG. 5, when weight of the display apparatus 14 is denoted as Wc, and a distance from the rotation axis X of the display apparatus 14 to a centroid G is denoted as rc, an amount of force Mmin at which the display apparatus 14 turns by the self-weight is a product of the weight Wc and the distance rc (Mmin=Wc·rc).

Here, let the amount of force Mmin at which the display apparatus 14 turns by the self-weight be, for example, 8 N·cm (Mmin=8 N·cm), and an amount of force Mmax at which the user as the operator can smoothly perform a turning operation of the display apparatus 14 be, for example, 30 N·cm.

That is, even when an amount of force M at which the display apparatus 14 is turned is generated within a range of Mmin<M<Mmax, the predetermined frictional force for making the display apparatus 14 stationary without turning should just be generated by the turn fixing mechanism portion 30.

As an example configuration of the turn fixing mechanism portion 30 for the purpose, as shown in FIG. 6, when a wire diameter d0 as the outer diameter of the frictional force generating member 33 which is an O-shaped ring is assumed to be, for example, 2±0.1 mm, a crushed amount h of the frictional force generating member 33 in the rotation axis X can be set to 0.26 mm<h<0.38 mm to generate the predetermined frictional force for making the display apparatus 14 stationary without turning through the turn fixing mechanism portion 30 as long as the amount of force M at which the display apparatus 14 is turned falls within the range of Mmin<M<Mmax.

Note that when a value obtained by dividing the crushed amount of the frictional force generating member 33 which is an O-shaped ring by the wire diameter d0 is defined as a crushing rate (compression rate), a tolerance of ±0.1 mm of the wire diameter d0 leads to a minimum crushing rate of 0.26/2.1≈0.12 when a tolerance of +0.1 mm is generated in the wire diameter d0 of the frictional force generating member 33 (d0=2.1 mm), and leads to a maximum crushing rate of 0.38/1.9=0.2 when a tolerance of −0.1 mm is generated in the wire diameter d0 of the frictional force generating member 33 (d0=1.9 mm). Accordingly, a proper range of the crushing rate (compression rate) of the frictional force generating member 33 is 12%-20%.

As described above, the endoscope apparatus 1 of the embodiment does not have a mechanism in which the turned position of the display apparatus 14 or the like is fixed by holding with conventional torque-managed screws, but has a structure in which the predetermined frictional force for making the display apparatus 14 stationary without turning is generated by the turn fixing mechanism portion 30.

Therefore, the endoscope apparatus 1 has a structure in which the turned position of the display apparatus 14 is more stably fixed than conventional ones, so that movement during use is prevented. The endoscope apparatus 1 has a structure in which it is not necessary to tighten or loosen a screw or the like when fixing the turned position of the display apparatus 14 or making turnable, and repulsive force is generated by the frictional force generating member 33 which is an elastic member provided in the turn fixing mechanism portion 30, so that backlash and the like due to aged deterioration and the like are less likely to occur.

Furthermore, the endoscope apparatus 1 has a structure in which the display apparatus 14 does not turn due to the self-weight, and the user as the operator can smoothly perform a turning operation of the display apparatus 14 by setting the crushed amount of the frictional force generating member 33 of the turn fixing mechanism portion 30 within a proper range.

As described above, the endoscope apparatus 1 has a structure in which the turn fixing mechanism portion 30 makes it possible to smoothly perform a turning operation of the display apparatus 14, which is a component turnably provided with respect to the operation portion 13, to a desired position, and enables stable fixation at the desired position.

Modification

Figure 7:
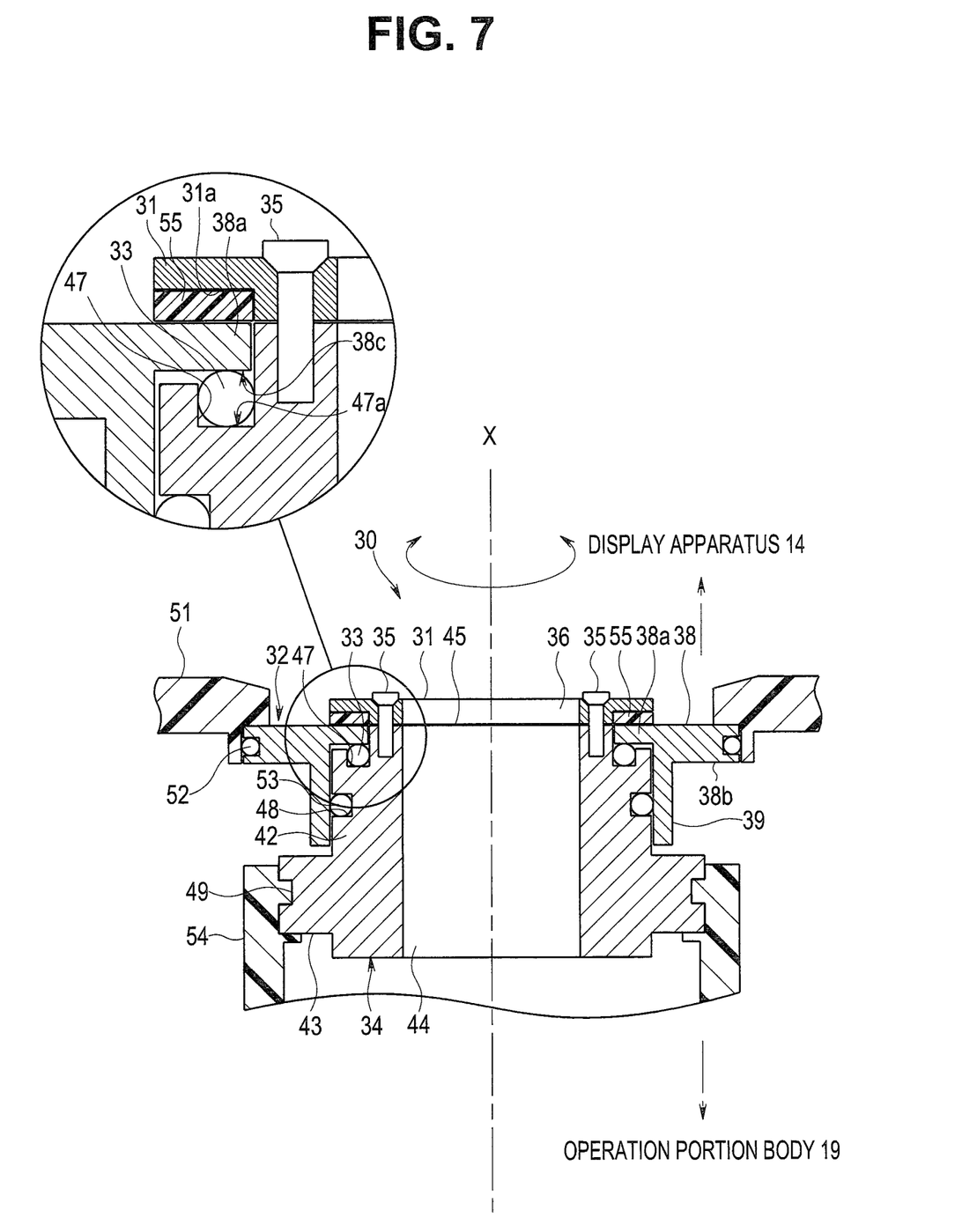
FIG. 7 is a sectional view showing a structure of a turn fixing mechanism portion in a modification of the endoscope apparatus.

FIG. 7 is a sectional view showing a structure of a turn fixing mechanism portion in a modification.

As shown in FIG. 7, the turn fixing mechanism portion 30 may have a structure in which a step portion 31a obtained by notching the lower surface of the holding member 31 in the circumferential direction is formed, and the step portion 31a is provided with a plate-shaped ring member 55 having good slipperiness such as a washer made of polyacetal serving as friction reducing means to reduce wear between components, which are the plate-like ring member 31 and the turning mount 32 here, due to turning of the display apparatus 14.

Note that generated frictional force is unstable in the turn fixing mechanism portion 30 unless it has been specified whether turning of the display apparatus 14 causes the frictional force generating member 33 to follow the turning mount 32 during turning to turn together, or to remain in a state of not moving together with the fixed mount 34. Therefore, an amount of turning force M of the display apparatus 14 is also unstable.

Therefore, it is preferable to change surface roughness Ra of a bottom surface 47a of the recessed portion 47 of the fixed mount 34 in contact with the frictional force generating member 33, and of a lower surface 38c of the inward flange portion 38a of the turning mount 32 to generate a difference between friction coefficients of portions in contact with the frictional force generating member 33.

As an example, the bottom surface 47a of the recessed portion 47 of the fixed mount 34 is finished to set the surface roughness Ra to 20-30, and the lower surface 38c of the inward flange portion 38a of the turning mount 32 is finished to set the surface roughness Ra to 1.0-2.0.

Thus, the frictional force generating member 33 no longer moves on the side of the recessed portion 47 of the fixed mount 34, and is specified only by frictional force with the inward flange portion 38a of the turning mount 32, so that the amount of turning force M of the display apparatus 14 can be stabilized.

Note that although the above description has exemplified the turn fixing mechanism portion 30 of the endoscope apparatus 1 provided in a structure in which the display apparatus 14 as the turning unit is turned with respect to the operation portion 13, no limitation is imposed, for example, the turn fixing mechanism portion 30 may be used for a tilt mechanism in which the monitor portion 3 serving as the turning unit with respect to the display apparatus 14 is raised, or may be used as a turn fixing mechanism portion 30 for a structure in which the insertion portion 12 as the turning unit is turned with respect to the operation portion 13.

Furthermore, although the O-shaped ring has been exemplified as the frictional force generating member 33, no limitation is imposed, and an elastic member such as a rubber packing or various springs may be used.

Although the above embodiment has exemplified a structure in which the display apparatus 14 is turnable around the turning axis X which is the axis in the longitudinal direction of the endoscope apparatus 1 (the operation portion body 19 of the operation portion 13), no limitation is imposed, and a structure is also possible in which the display apparatus 14 is turnable around an axis having a predetermined angle with respect to the longitudinal direction of the endoscope apparatus 1. It suffices to provide a structure in which the turn fixing mechanism portion 30 makes it possible to smoothly perform a turning operation of the display apparatus 14 to a desired position, and stably fixes the display apparatus 14 at the desired position.

The invention described in each above embodiment is not limited to the embodiment and the modification, and it is possible to implement various other modifications in implementation stages within a range not departing from the gist. Furthermore, each above embodiment includes inventions at various stages, and a plurality of disclosed components can be combined appropriately to extract various inventions.

For example, even if some components are deleted from all components shown in each embodiment, a configuration in which the components are deleted can be extracted as an invention when the described problem can be solved and the described effect can be obtained.

According to the present invention, it is possible to provide a turn fixing mechanism portion of an endoscope apparatus which makes it possible to smoothly perform a turning operation of a turnably provided component to a desired position, and stably fixes the component at the desired position, and to provide the endoscope apparatus.

What is claimed is:

1. An endoscope apparatus comprising:
a turn fixing mechanism portion comprising:
- a turning portion configured to be turnable, and being connected to a display, the turning portion including a first hole;
- a fixed portion including a projecting portion configured to be inserted into the first hole, and a recessed portion formed around the projecting portion, the recessed portion having a predetermined depth;
- an elastic member disposed in the recessed portion and held between the recessed portion and the turning portion;
- a holding member configured to fix a turned position of the display by pressing the turning portion toward a side of the fixed portion to cause the turning portion to abut the projecting portion, and by compressing the elastic member by the turning portion by a predetermined amount to generate a predetermined frictional force;
- a second hole formed at the holding member; and
- a fastening member configured to be inserted into the second hole, and to fix the holding member to the projecting portion;

an operation portion having a first portion on which the display is turnably disposed;
an insertion portion connected to the operation portion at a second portion of the operation portion, the second portion being different from the first portion.

2. The endoscope apparatus according to claim 1, wherein the elastic member is an O-shaped ring.

3. The endoscope apparatus according to claim 1, further comprising a friction reducing member provided between the holding member and the turning portion.

4. The endoscope apparatus according to claim 1, wherein the predetermined amount is a compression rate of 12%-20% of an outer diameter of the elastic member.

* * * * *